United States Patent
Obradovic

(10) Patent No.: US 10,864,071 B2
(45) Date of Patent: Dec. 15, 2020

(54) STENT GRAFT

(71) Applicant: Nikola Obradovic, Lorrach (DE)

(72) Inventor: Nikola Obradovic, Lorrach (DE)

(73) Assignee: Bentley InnoMed GmbH, Hechingen (DE)

( * ) Notice: Subject to any disclaimer, the term of this patent is extended or adjusted under 35 U.S.C. 154(b) by 0 days.

(21) Appl. No.: 15/565,736

(22) PCT Filed: Apr. 20, 2016

(86) PCT No.: PCT/EP2016/058694
§ 371 (c)(1),
(2) Date: Oct. 11, 2017

(87) PCT Pub. No.: WO2016/169949
PCT Pub. Date: Oct. 27, 2016

(65) Prior Publication Data
US 2018/0116782 A1 May 3, 2018

(30) Foreign Application Priority Data
Apr. 21, 2015 (DE) .................. 10 2015 106 052

(51) Int. Cl.
*A61F 2/07* (2013.01)
*A61F 2/915* (2013.01)
*A61F 2/958* (2013.01)

(52) U.S. Cl.
CPC ............. *A61F 2/07* (2013.01); *A61F 2/915* (2013.01); *A61F 2/958* (2013.01); *A61F 2002/072* (2013.01); *A61F 2002/075* (2013.01); *A61F 2002/91575* (2013.01); *A61F 2210/0014* (2013.01); *A61F 2220/005* (2013.01); *A61F 2220/0091* (2013.01)

(58) Field of Classification Search
None
See application file for complete search history.

(56) References Cited

U.S. PATENT DOCUMENTS

| | | | |
|---|---|---|---|
| 2002/0049493 A1* | 4/2002 | Jang | A61F 2/91 623/1.16 |
| 2013/0317595 A1* | 11/2013 | Obradovic | A61F 2/07 623/1.13 |

FOREIGN PATENT DOCUMENTS

| | | |
|---|---|---|
| DE | 102012001996 A1 | 8/2013 |
| JP | 2002-515781 A | 5/2002 |

(Continued)

OTHER PUBLICATIONS

Brazilian Office Action dated May 12, 2020 in connection with related Brazilian Patent Appl. No. BR112017022496-8.

(Continued)

*Primary Examiner* — Megan Y Wolf
(74) *Attorney, Agent, or Firm* — Brooks Kushman P.C.

(57) ABSTRACT

Stent graft comprising a stent (1) having a plurality of ring segments (3) arranged side by side and connected with each other by connecting webs (7) having a meandering pattern, and at least one membrane (2), characterized in that a plurality of connecting webs (7) between adjacent ring segments (3) are provided with flexible tongues (6), which are arranged in a form-closed manner in the connecting webs (7) and which are resiliently movable against the connecting webs (7), wherein the membrane (2) being clamped between flexible tongues (6) and connecting webs (7).

12 Claims, 3 Drawing Sheets

(56) References Cited

FOREIGN PATENT DOCUMENTS

Figure 1:
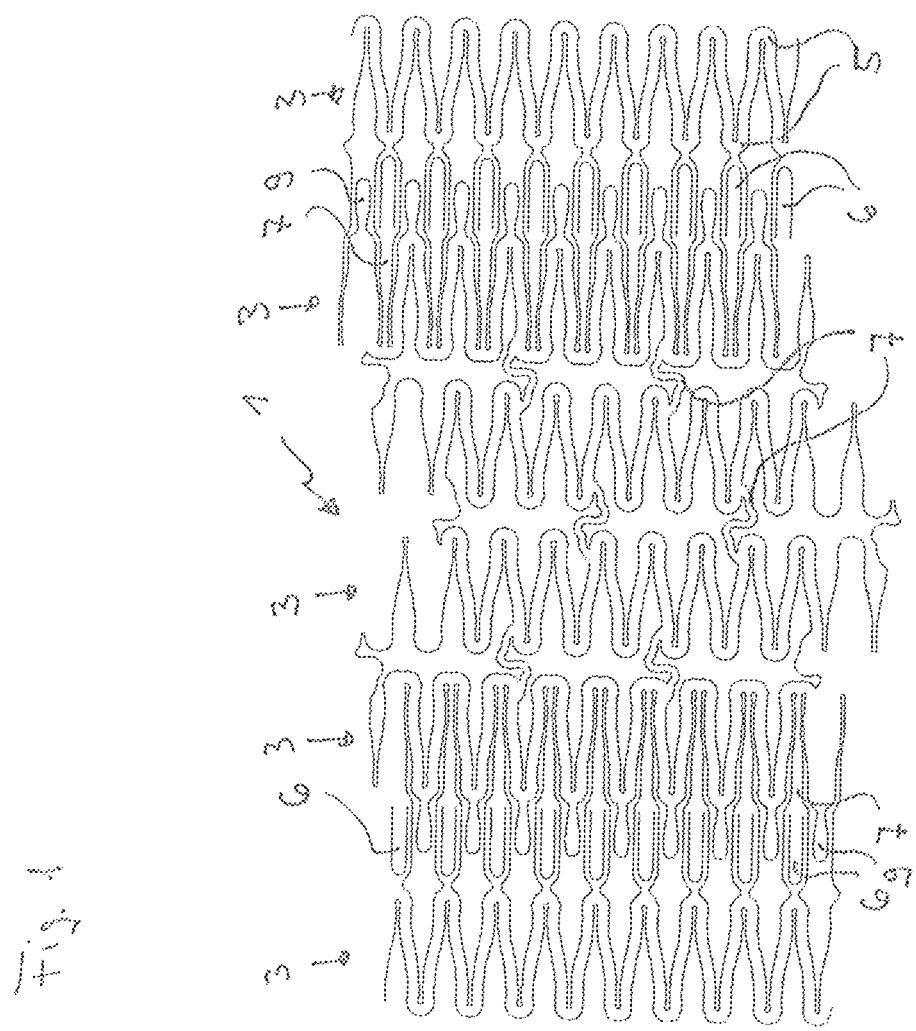

JP  2014-503276 A  2/2014
WO  WO2005/087138 A1  9/2005

OTHER PUBLICATIONS

Japanese Office Action dated Feb. 19, 2020 in connection with related Japanese Patent Appl. No. 2017-555699.

* cited by examiner

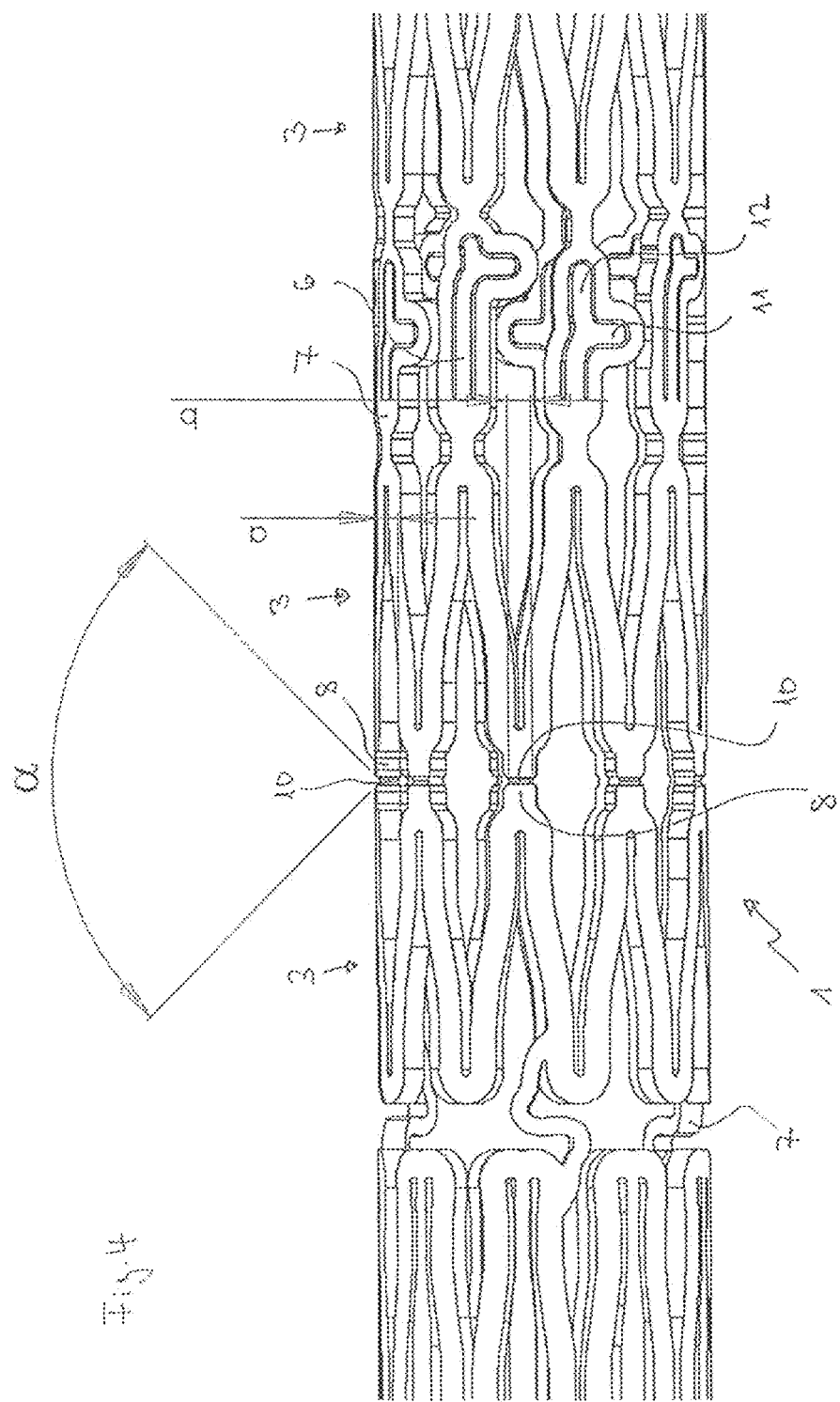

STENT GRAFT

The invention relates to a stent graft consisting of a stent with a plurality of ring segments arranged side by side and connected with each other by connecting webs, and at least one membrane. Moreover, the invention also relates to the use of such a stent graft with a view to treating vascular malformations.

Stent grafts of this type are used in blood vessels, e.g. to give support to abnormally narrowed, dilated or damaged blood vessels. The combination of stent and membrane is also used to treat extended, vascular sections in need of treatment and requiring an implant of greater length and, above all, flexibility. In particular, stent grafts are employed to bridge vascular malformations, for example to isolate aneurysms from the blood circulation. Balloon catheters are usually used for the implantation of such stent grafts State-of-the-art stent grafts consisting of two stents and a flexible membrane, such as Teflon, are known to be used for this task. Such a stent graft is described in publication EP 2 151 217 A1. The disclosed stent graft consists of an inner stent and an outer stent arranged coaxially around this first one, between which a flexible, expandable membrane is arranged. The end areas of the stents with the membrane located in between are welded together.

Publication EP 1 266 635 A2 discloses a stent graft comprising a cylindrical stent and a cylindrical membrane, which are, for example, connected to each other by seams or hooks. In addition or alternatively, the connection can be secured by a slight overlap of stent and membrane.

WO 2009/035679 A1 discloses a stent graft being provided with a continuous inner liner made of polyester or ePTFE. A stent is arranged at one area of this inner liner and encloses the inner liner coaxially. The areas of the inner liner adjacent to the stent are coated with a second layer of polyester or ePTFE to increase the wall thickness of the implant in the area not supported by the stent. The end areas of the stent and the second layer are pushed against each other. If necessary, additional reinforcing material, e.g. ePTFE, can be applied to the outside of the stent graft components, especially at the transitions between the stent and the second layer.

Of the above-mentioned stent grafts providing for a membrane connecting to a stent, only the stent graft shown in EP 1 266 635 A2 connects exactly one stent with exactly one membrane. The other prior-art solutions always require another stent or another membrane arranged coaxially around the first stent or membrane for reinforcement purposes.

The solution according to EP 1 266 635 A2 uses hooks or threads and/or alternatively an overlap of both components for the connection between stent and membrane. In this respect, the durability of the hooks and threads, which are exposed to high frictional forces within the blood vessel, is always problematic. Moreover, there is also the risk of tissue irritation or injury as a result of sticking out hooks or protruding edges between the stent and membrane.

Stent grafts are also described in WO 2012/084202 A1 and WO 01/66035 A2. In this case, the membrane is fixed at the peripheral ring segments, which means that the expansion of the stent during placement can impair the fixation of the membrane on the stent.

It is, therefore, the task of the present invention to propose a stent graft that simply and durably connects the stent and membrane, consumes very little vascular lumen and does not cause tissue irritation or injury. In particular, the connection between the membrane and the stent should not be provided at the ring segments in order to ensure a secure fixation of the membrane.

This objective is achieved by the invention by proposing a stent graft of the kind first mentioned above, in which a plurality of connecting webs between adjacent ring segments are provided with flexible tongues, which are arranged in a form-closed manner in the connecting webs and which are resiliently movable against the connecting webs, wherein the membrane being clamped between flexible tongues and connecting webs.

The stent graft proposed by the invention consists of a plurality of interconnected meandering ring segments. These ring segments correspond to the ring segments of conventional stents, as they are often suggested and used. In accordance with the present invention, connecting webs between two ring segments are designed and modified, with flexible tongues being cut into said connecting webs. The connecting webs with flexible tongues connect in particular peripheral ring segments with adjacent ring segments.

By peripheral ring segments, ring segments are to be understood that are arcs ranged at the end of the stent, that is, which limit the stent at its ends. According to the invention, only one of these peripheral ring segments may be connected to the adjacent ring segment via connecting webs with flexible tongues, but preferably these are the peripheral ring segments at both ends of the stent.

A meandering web run of the peripheral ring segments is understood to mean both a wavelike web run and a zigzag-shaped web run. Wavelike and zigzag-shaped web runs and ring segments are commonly used for vascular stents in order to at least partially compensate for the length contraction that occurs during expansion.

In order to form the flexible tongues, the connecting webs are partially incised so that flexible tongues are created that are movable against and with respect to the web extension. Either inwards or outwards pointing flexible elements can be produced by the incisions. In the manufactured state of the stent (i.e. before being crimped onto a balloon or before expansion), the flexible tongues themselves are fitted into the webs in a form-closed manner.

In order not to deteriorate the strength of the webs by making incisions into the connecting webs, it is advisable to increase the web width in the area of the flexible tongues, that is, double or triple it, for example. This means that the flexible tongues can have a substantially normal web width, same as the web elements of the connecting webs arranged adjacent to the side of the flexible tongues.

The attachment of the membrane by means of flexible tongues arranged next to each other on the stent enables an easy and safe connection of stent and membrane. The flexible tongues arranged in the web loops are produced by laser cutting, for example. Clamping of the membrane under the flexible tongues is, from a manufacturing point of view, easy to achieve. The integration of the connecting elements between the stent and the membrane in the form of flexible tongues into the stent eliminates the danger that the connecting components detach from the stent and are allowed to move freely in the bloodstream, as may be encountered with other connecting elements. At the same time, this type of integration rules out that a stent expansion impairs the membrane fixation.

To achieve a consistent connection between stent and membrane, it is advisable to arrange side by side a larger number of flexible tongues pointing in the same direction. In particular, all connecting webs of the respective peripheral ring segment pointing in the same direction are provided with a flexible tongue. These flexible tongues are then aligned parallelly to the longitudinal axis of the stent, preferably pointing out of the stent. In this case, the shape of the flexible tongues largely corresponds to the shape of the connecting webs.

As a rule, the flexible tongues are aligned parallelly to the longitudinal axis of the stent. Deviations from parallelism are also possible, however, if the incisions and configuration of the connecting webs are designed accordingly.

The number of flexible tongues between two peripheral ring segments basically depends on the desired strength of the respective connection made between stent and membrane. As a rule, at least two oppositely arranged connecting webs of a peripheral ring segment will be equipped with flexible tongues, preferably all connecting webs of the peripheral ring segment attaching to the adjacent ring segment.

The stent graft proposed by the present invention will usually comprise a stent that can be expanded by means of a balloon catheter, for example, a stent made of medically acceptable steel. Alternatively, it is also possible to use variants providing for the stent to be of self-expanding design, e. g. by using a shape-memory alloy such as nitinol.

The membrane, usually consisting of a film or a tube, can consist of any desired material as it is customarily employed and approved in the medical field. However, PTFE and polyester are particularly suitable. Especially preferred is a membrane made of ePTFE. The membrane can also be functionally coated, for instance with anti-inflammatory, proliferation-inhibiting or therapeutic substances such as rapamycin, paclitaxel or heparin, for example. The membrane is preferably tubular in shape and has the required elongation capability to go along with the stent expansion.

The flexible tongues of the connecting webs of the peripheral ring segments with a meandering web configuration can be oriented stent-inwards or outwards and preferably point in the direction out of the stent. The membrane clamped into the flexible tongues can be folded back on itself to improve the seating in the end area, which comes underneath the flexible tongues, in order to achieve a better clamping effect.

On the inventive stent graft the membrane can be arranged inside or outside. The preferred arrangement of the membrane is on the outer side. The advantage of this arrangement is that the effect of the stent structure on the vessel wall is diminished due to the membrane being located between them. In particular, the membrane is clamped to the peripheral ring segments at both ends of the stent.

It is also possible to have a variant in which the membrane is clamped inside the stent into the flexible tongues, extends outside over the stent surface and is held again inside by the flexible tongues at the opposite end. In this case, the flexible tongues preferably point into a direction outwards of the stent. Similarly, the membrane can be arranged on the inside of the stent and clamped onto the outside and a combination of external and internal clamping is also possible.

Preferably, the membrane is additionally fixed at the peripheral ring segments by gluing/bonding. This can be done with a biocompatible adhesive, but preferably with an adhesive tape that is stuck over the membrane at the location of the flexible tongues. In addition to the securing aspect, such an adhesive tape also serves to protect the vessel wall from having direct contact with the flexible tongues of the peripheral ring segment.

The stent grafts according to the invention can have the membrane arranged at an arbitrary position and also comprise more than one membrane. For example, the membrane may only be located at one or the other end of the stent or in the middle of the stent, leaving certain stent areas free. Furthermore, it is also possible to provide more than just one membrane, said membranes being, for example, arranged at the ends with a certain amount of space left uncovered. If there is more than just one membrane, each one is secured separately by means of appropriate flexible tongues and, if considered expedient, by sticking it to the stent framework.

For example, if two membranes are arranged at the ends, the interjacent part of the stent graft that is not covered by a membrane can be positioned in the region of a vessel junction, so that the blood flow into the branching vessel is not impaired. For this purpose, the two stent halves that are covered by the membrane may only be loosely attached to each other by so-called connectors. In this way, increased flexibility is also achieved in this area.

With a view to increasing their flexibility, stents, especially the stent grafts proposed by the invention, may also be provided with notches. Said notches are preferably arranged on the connecting webs between two ring segments. Expediently, connecting webs provided with notches should not have flexible tongues. In particular, the notches allow the stent grafts to be adapted to a curved vessel configuration and to an end of the stent widened so as to have a trumpet-like shape in the event of so-called fenestrations. For fenestrations, stents are arranged in branches originating from a main vessel which has also been provided with a stent and said stents being connected via a "window" existing in the stent provided in the main vessel. Such fenestrations are required, for example, in the case of aortic aneurysms that have to be bridged by a stent and in which an outgoing vessel must be kept free and also be provided with a stent.

The notches are conveniently located on old connecting webs between the respective ring segments. A stent graft can also be provided with multiple notches over its extension, that is, between more than just two ring segments. The indentations can be "real" notches with an opening angle of, for example, 60° to 120°, such notches having straight legs, but may also have rounded depressions, approximately of semicircular shape. The indentation should have a depth of not more than about ⅓ of the web thickness, in particular not more than ¼. The web width may also be reduced in the indentation area, for example by ¼ compared to the normal web width. In any case, the depression is considerably smaller than the web width and amounts to a maximum of ¼ of the web width.

The stent grafts proposed in accordance with the invention are primarily used for the treatment of vascular malformations. This may involve the closure of diverging or branching vessels, but also the occlusion of aneurysms or arteriovenous shunts.

Moreover, it is also possible to provide embodiments in which the inventive stent graft comprises two stent units that serve to clamp an intermediate tubular membrane into a vessel. In this case, the stent has the clamp connection for the fixation of the membrane only at one end; the other end of the tubular membrane being connected to the second stent. Such a stent graft can be implanted into extensively damaged vessels, for example after obliteration of the epithelial cell layer of a blood vessel.

According to a particularly preferred embodiment, the flexible tongues arranged in the connecting webs may form in their end area or in their configuration a bend or branching in such a way that they describe, for example, a right angle. In this way, a larger contact area is brought about between the flexible tongue and the clamped-in membrane, which improves the fixation effect of the flexible tongues. In this case as well, the form-closed fitting of the flexible tongues in the connecting webs remains unchanged, with free movement against and relative to the extension of the connecting webs. In the developed area, the connecting webs accordingly show a curve extending around the angled end area of the flexible tongue.

As per a further preferred embodiment, at least one of the two ring segments between which the connecting webs with the flexible tongues extend may have freely ending webs which are aligned parallelly to the flexible tongues. These webs are arranged at the tips or turning points of the ring segments and also provide flexibility due to a resilient effect since their ends are allowed to terminate freely. The membrane can then be arranged alternately above and below the flexible tongues in the connecting webs and the freely ending webs. This also increases the contact surface with the clamped-in membrane and thus serves to secure the membrane on the stent.

Figure 2:
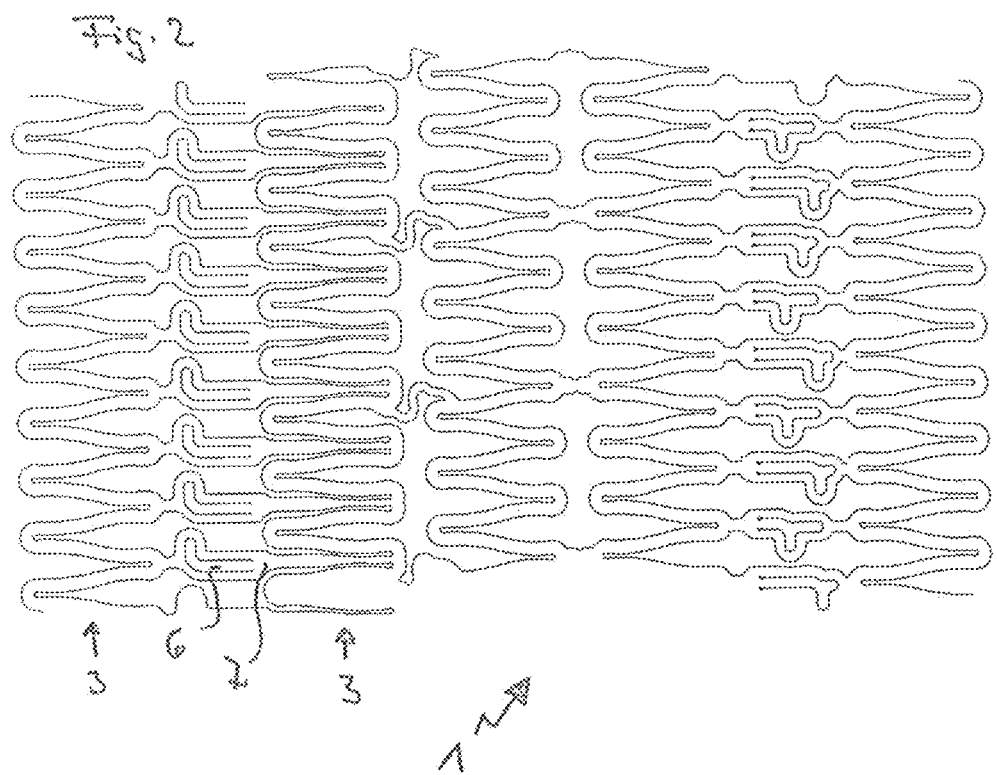
Figure 3:
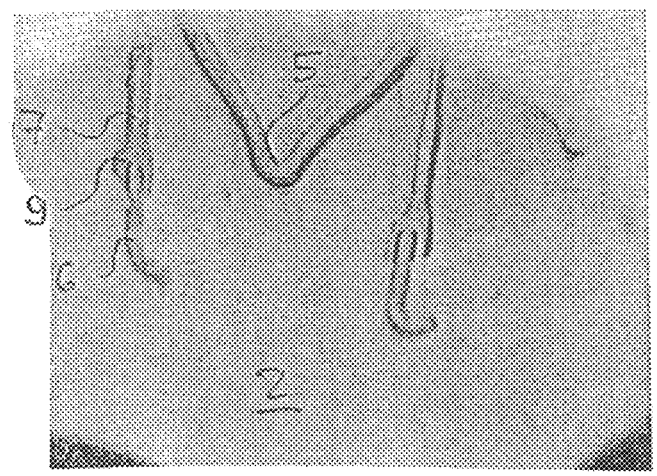

Further elucidation of the invention is provided through the enclosed figures, where FIG. 1 shows a first stent modified in accordance with the invention, FIG. 2 shows a second stent modified in accordance with the invention, and FIG. 3 illustrates the stent according to FIG. 2 with membrane clamped in place, and FIG. 4 shows a stent provided with notches FIG. 1 shows a stent 1 altered in accordance with the invention, as it has been modified for the fixation of a membrane via flexible tongues 6. Stent 1 consists of a plurality of ring segments 3, which have an essentially zigzagging configuration. In the figure, stent 1 is illustrated in its cut-open and spread-out state; in its original state after manufacture it consists of a tube composed of webs and provided with perforations, for example fabricated of medical steel or nitinol. Stent fabrication is carried out in a way that is known per se by laser cutting of a suitably dimensioned tube.

The ring segments 3 are interconnected by expansion elements 7 in such a way that when the stent is placed over a balloon, the length reduction resulting from the expansion of the ring segments 3 is at least partially compensated by an elongation of the connecting elements 7.

The peripheral ring segment 3 at the end of the stent has a meandering configuration. A zigzagging pattern would also be possible. The individual webs form web loops 5, which extend in the form of waves or meanders over the circumference of the stent.

The connecting webs 7 originating from the peripheral ring segments 3, are provided with incisions that allow flexible tongues 6 to form, which are resiliently movable against the general extension of webs 7. This makes it possible to insert a membrane between the flexible tongues 6 and the surrounding connecting webs 7, said membrane being held in place by clamping. Furthermore, it is to be understood that the connecting webs between the individual ring segments may be of considerably varying design, for example elongated between a peripheral ring segment and the neighboring ring segment and curved between ring segments located in a middle position.

The design according to FIG. 1 also shows freely ending webs 9, which start from web loops 5 and are aligned parallelly to connecting webs 7 with the flexible tongues 6. These freely ending webs 9 are also movable in the same direction as the flexible tongues 6 against the extension or run of connecting webs 7 and ring segments 3. A membrane can be clamped alternately between the tongues 6 and the freely ending webs 9 in such a way that the membrane is positioned below tongues 6 and above the freely ending webs 9. The webs 9 improve the fixation of the membrane on the stent.

FIG. 2 illustrates a preferred variant of a stent graft proposed by the invention. In this variant, the flexible tongues 6, which are arranged in connecting webs 7 between the peripheral segments 3, have an angled configuration. As shown, the flexible tongues 6 thus have a hook-shaped design but are still fitted into the connecting web 7 in a form-closed manner. In the area of the angular offset, the connecting web 7 has a semicircular curvature which includes the angled part of the flexible tongue 6. The flexible tongue 6 is still resiliently movable against and in relation to the extension of the connecting web. The flexible tongue and adjacent web elements have essentially the same width.

This special configuration of flexible tongue 6 brings about a larger contact surface for the clamped membrane and thus serves to secure the membrane by preventing it from slipping.

FIG. 3 shows the stent according to FIG. 2 with membrane clamped in place. Illustrated is web loop 5 of the ring segment from which the connecting web originates, the fork 10 of the connecting web 7 with the attachment of the flexible element 6 and the offset end of the flexible element 6. The membrane 2 is clamped in place between the connecting webs 7 in the forked area and the flexible tongue 6 in such a way that flexible tongue 6 essentially rests on the membrane and securely holds it against the connecting web 7 extending below.

FIG. 4 shows a stent 1 to be used as proposed by the invention with notches 10. The notches 10 are located on the outside of connecting webs 8 between two ring segments 3 which do not have flexible tongues 6. The notches 10 are provided with straight legs having an opening angle α of 90° and a depth of about ⅕ of the web thickness of the connecting webs 8. The web width b of the connecting webs 8 is reduced by about ¼ in the area of notch 10, a indicates the reduced thickness of the connecting webs 8 in the area of notches 10.

FIG. 4 also depicts a variant of flexible tongues 6 in the connecting webs 7 between a peripheral segment 3 and an adjacent ring segment 3. The flexible tongues 6 in this case have an angled end 11 (90°) with a nose 12 located in the area of the angular offset pointing to the end of the stent.

The inventive stent graft is crimped onto a balloon catheter in a customary manner and expanded at the placement site using conventional techniques. During this, the stent 1 with the membrane 2 touches the vessel wall. The membrane 2 is located between the stent 1 and the vessel wall.

The invention claimed is:

1. Stent graft comprising a stent (1) having a plurality of ring segments (3) the ring segments having a meandering pattern and being arranged side by side, adjacent ring segments (3) being connected with each other by connecting webs (7), the stent graft further comprising at least one membrane (2), characterized in that a plurality of connecting webs (7) between two adjacent ring segments (3) are provided with flexible tongues (6), which are arranged in a form-closed manner in the connecting webs (7) and which are resiliently movable with respect to the connecting webs (7), wherein the at least one membrane (2) is clamped between the flexible tongues (6) and the connecting webs (7), and wherein at least one of the two adjacent ring segments (3) between which the connecting webs with flexible tongues extend has freely ending webs which are aligned in parallel to the flexible tongues and are arranged at turning points of the at least one of the two adjacent ring segments, each of the freely ending webs (9) projecting into a gap between two connecting webs (7), said freely ending webs (9) serving to additionally secure the at least one membrane (2).

2. Stent graft according to claim 1, characterized in that the flexible tongues (6) point out of the stent.

3. Stent graft according to claim 2, wherein the at least one membrane (2) is in the form of a tube.

4. Stent graft according to claim 3, characterized in that the tube covers the outside of the stent (1).

5. Stent graft according to claim 4, characterized in that the tube has an edge region clamped in place via the flexible tongues (6), the edge region being folded inwardly.

6. Stent graft according to claim 1, characterized in that the at least one membrane (2) is secured in the flexible tongues (6) by additional bonding with adhesive tape.

7. Stent graft according to claim 1, characterized by a plurality of membranes (2) arranged in sections, each of which is secured to flexible tongues (6).

8. Stent graft according to claim 1, characterized in that the at least one membrane (2) consists of an ePTFE tube.

9. Stent graft according to claim 1, characterized in that the stent (1) is a balloon-expandable stent.

10. Stent graft according to claim 9 capable of being crimped onto a balloon of a balloon catheter.

11. Stent graft according to claim 1 wherein the stent is self-expanding and made of a shape-memory alloy.

12. Stent graft according to claim 1, characterized in that the flexible tongues (6) have a free end and are of angled configuration at their free end or have a branch (11) in their configuration.

* * * * *